(12) United States Patent
Haines et al.

(10) Patent No.: US 9,820,751 B2
(45) Date of Patent: Nov. 21, 2017

(54) SURGICAL DRAPE CONFIGURED FOR PERIPHERALLY INSERTED CENTRAL CATHETER PROCEDURES

(75) Inventors: Kimberly Haines, Deerfield, IL (US); Debbie Esquivel, Lindenhurst, IL (US)

(73) Assignee: Medline Industries, Inc., Northfield, IL (US)

( * ) Notice: Subject to any disclaimer, the term of this patent is extended or adjusted under 35 U.S.C. 154(b) by 1362 days.

(21) Appl. No.: 13/116,473

(22) Filed: May 26, 2011

(65) Prior Publication Data

US 2012/0298116 A1    Nov. 29, 2012

(51) Int. Cl.
| | | |
|---|---|---|
| *A61B 19/08* | (2006.01) |
| *A61B 17/132* | (2006.01) |
| *A61B 46/00* | (2016.01) |
| *A61B 46/20* | (2016.01) |

(52) U.S. Cl.
CPC .......... *A61B 17/1322* (2013.01); *A61B 46/00* (2016.02); *A61B 2046/201* (2016.02); *A61B 2046/205* (2016.02)

(58) Field of Classification Search
USPC .................. 128/853, 849, 854, 852, 855
See application file for complete search history.

(56) References Cited

U.S. PATENT DOCUMENTS

| | | |
|---|---|---|
| 371,353 A | 10/1887 | Perry |
| 850,960 A | 4/1907 | O'Connoor |
| 1,506,332 A | 8/1924 | Bloom |
| 1,980,435 A | 11/1934 | Reagan |
| 2,172,162 A | 8/1939 | Gillette |
| 2,430,941 A | 11/1947 | Long |
| 2,653,324 A | 8/1953 | McMahon |
| 2,673,347 A | 3/1954 | Weiss |
| 2,825,902 A | 3/1958 | Breier |
| 3,130,462 A | 4/1964 | Mitchell |
| 3,144,661 A | 8/1964 | Buser |
| 3,276,036 A | 10/1966 | Carter et al. |
| 3,359,569 A | 12/1967 | Scrivens |
| 3,397,406 A | 8/1968 | Leach |
| 3,399,406 A | 9/1968 | Bradley |
| 3,429,433 A | 2/1969 | Holt |
| 3,451,062 A | 6/1969 | Bradley |

(Continued)

FOREIGN PATENT DOCUMENTS

| | | |
|---|---|---|
| DE | 8904426 | 5/1989 |
| DE | 202006005966 | 10/2006 |

(Continued)

OTHER PUBLICATIONS

Lee, Cheol Soo "International Search Report", PCT/US2012/032122; Filed Apr. 4, 2012; Mailed Nov. 1, 2012.

(Continued)

*Primary Examiner* — Victoria J Hicks
(74) *Attorney, Agent, or Firm* — Philip H. Burrus, IV

(57) ABSTRACT

A medical drape (100) includes an upper portion (101) and a lower portion (102). The upper portion (101) can be pellucid, while the lower portion (102) can be opaque. To facilitate central catheter insertion, the upper portion (101) can define one or more apertures (104,105) through which a central line may be inserted. A tourniquet (401) may be integrated with the drape, as can one or more tool-less removal features (108,109).

16 Claims, 11 Drawing Sheets

(56) References Cited

U.S. PATENT DOCUMENTS

| | | | |
|---|---|---|---|
| 3,540,441 | A | 11/1970 | Collins |
| 3,625,206 | A | 12/1971 | Charnley |
| 3,696,443 | A | 10/1972 | Taylor |
| 3,707,964 | A | 1/1973 | Patience et al. |
| 3,721,999 | A | 3/1973 | Goya et al. |
| 3,750,664 | A | 8/1973 | Collins |
| 3,803,640 | A | 4/1974 | Ericson |
| 3,858,243 | A | 1/1975 | Pierron et al. |
| 3,881,474 | A | 5/1975 | Krzewinski |
| 3,881,476 | A * | 5/1975 | Bolker et al. ............... 128/855 |
| 3,935,596 | A | 2/1976 | Allen, Jr. et al. |
| 3,952,373 | A | 4/1976 | Noorily |
| 3,956,048 | A | 5/1976 | Nordgren |
| 3,968,792 | A | 7/1976 | Small |
| 3,989,040 | A | 11/1976 | Lofgren et al. |
| 4,000,521 | A | 1/1977 | Zoephel et al. |
| 4,017,909 | A | 4/1977 | Brandriff |
| 4,041,942 | A | 8/1977 | Dougan et al. |
| 4,119,093 | A | 10/1978 | Goodman |
| 4,134,398 | A | 1/1979 | Scrivens |
| 4,153,054 | A | 5/1979 | Boone |
| 4,214,320 | A | 7/1980 | Belkin |
| RE30,520 | E | 2/1981 | Pierron |
| 4,266,663 | A | 5/1981 | Geraci |
| 4,290,148 | A | 9/1981 | Roberts |
| 4,308,864 | A | 1/1982 | Small et al. |
| 4,323,062 | A | 4/1982 | Canty |
| 4,334,529 | A | 6/1982 | Wirth |
| 4,384,573 | A | 5/1983 | Elliott |
| 4,476,860 | A | 10/1984 | Collins et al. |
| 4,479,492 | A | 10/1984 | Singer |
| 4,489,720 | A | 12/1984 | Morris et al. |
| 4,523,335 | A | 6/1985 | Scrivens |
| 4,553,538 | A | 11/1985 | Rafelson |
| 4,561,126 | A | 12/1985 | Truman |
| 4,569,341 | A | 2/1986 | Morris |
| 4,596,245 | A | 6/1986 | Morris |
| 4,616,642 | A | 10/1986 | Martin et al. |
| 4,627,427 | A | 12/1986 | Arco |
| 4,631,756 | A | 12/1986 | Scrivens |
| 4,664,103 | A | 5/1987 | Martin et al. |
| 4,674,132 | A | 6/1987 | Stein et al. |
| 4,705,171 | A | 11/1987 | Eldridge |
| 4,711,236 | A | 12/1987 | Glassman |
| 4,745,915 | A | 5/1988 | Enright et al. |
| 4,783,854 | A | 11/1988 | Bjorklund |
| 4,829,602 | A | 5/1989 | Harreld et al. |
| 4,869,271 | A | 9/1989 | Idris |
| 4,905,710 | A | 3/1990 | Jones |
| 4,920,578 | A | 5/1990 | Janzen et al. |
| 4,942,987 | A | 7/1990 | Stackhouse |
| 4,951,318 | A | 8/1990 | Harreld et al. |
| 5,010,592 | A | 4/1991 | Skiles, Jr. |
| 5,029,344 | A | 7/1991 | Shannon et al. |
| 5,033,115 | A | 7/1991 | Bowling et al. |
| 5,042,507 | A | 8/1991 | Dowdy |
| 5,061,246 | A | 10/1991 | Anapliotis |
| 5,074,316 | A | 12/1991 | Dowdy |
| 5,097,534 | A | 3/1992 | Viemeister et al. |
| 5,109,873 | A | 5/1992 | Marshall |
| 5,135,188 | A | 8/1992 | Anderson et al. |
| 5,136,758 | A | 8/1992 | Wilcox et al. |
| 5,140,996 | A | 8/1992 | Sommers et al. |
| 5,345,946 | A | 9/1994 | Butterworth et al. |
| 5,362,306 | A | 11/1994 | McCarver et al. |
| 5,372,589 | A | 12/1994 | Davis |
| 5,377,387 | A | 1/1995 | Freed |
| D356,204 | S | 3/1995 | Derrickson |
| 5,410,758 | A | 5/1995 | Dupont et al. |
| 5,414,867 | A | 5/1995 | Bowling et al. |
| 5,417,225 | A | 5/1995 | Rubenstein et al. |
| 5,444,873 | A | 8/1995 | Levin |
| 5,533,209 | A | 7/1996 | Davis |
| 5,605,534 | A | 2/1997 | Hutchison |
| 5,611,356 | A | 3/1997 | Rothrum |
| 5,674,189 | A | 10/1997 | McDowell et al. |
| 5,707,703 | A * | 1/1998 | Rothrum et al. ............ 428/40.1 |
| 5,765,566 | A | 6/1998 | Rothrum |
| 5,778,889 | A | 7/1998 | Jascomb |
| 5,778,891 | A | 7/1998 | McMahan |
| 5,784,718 | A | 7/1998 | Finnegan |
| 5,816,253 | A | 10/1998 | Sosebee |
| 5,862,525 | A | 1/1999 | Tankersley et al. |
| 5,867,825 | A | 2/1999 | Scheerer |
| 5,916,202 | A | 6/1999 | Ilaswell |
| 5,973,450 | A | 10/1999 | Nishizawa et al. |
| 5,975,082 | A | 11/1999 | Dowdy |
| 5,985,395 | A | 11/1999 | Comstock et al. |
| 6,049,907 | A | 4/2000 | Palomo |
| 6,062,444 | A | 5/2000 | Tankersley et al. |
| 6,105,579 | A | 8/2000 | Levitt et al. |
| 6,115,840 | A | 9/2000 | Hastins |
| 6,138,278 | A | 10/2000 | Taylor |
| 6,196,033 | B1 | 3/2001 | Dowdle |
| 6,216,270 | B1 | 4/2001 | Moquin et al. |
| 6,244,268 | B1 | 6/2001 | Annett |
| 6,272,685 | B1 | 8/2001 | Kumar |
| 6,285,611 | B1 | 9/2001 | Kang |
| 6,345,622 | B1 | 2/2002 | Chandler et al. |
| 6,378,136 | B2 | 4/2002 | Matsushita |
| 6,405,730 | B2 | 6/2002 | Levitt et al. |
| 6,536,636 | B1 | 3/2003 | McDonniel |
| 6,564,386 | B2 | 5/2003 | Fujikawa et al. |
| 6,694,981 | B2 | 2/2004 | Gingles et al. |
| 6,742,522 | B1 | 6/2004 | Baker et al. |
| 6,820,622 | B1 | 11/2004 | Teves et al. |
| 6,843,252 | B2 | 1/2005 | Harrison et al. |
| 7,114,500 | B2 | 10/2006 | Bonutti |
| D533,982 | S | 12/2006 | Graneto, III |
| 7,181,773 | B1 | 2/2007 | Piraka |
| 7,237,271 | B1 | 7/2007 | McLandrich |
| 7,290,547 | B2 | 11/2007 | Hare et al. |
| 7,293,654 | B1 | 11/2007 | Wilson et al. |
| 7,305,991 | B2 | 12/2007 | Santilli et al. |
| 7,412,728 | B2 | 8/2008 | Alesina et al. |
| D579,178 | S | 10/2008 | Snyder et al. |
| 7,454,798 | B2 | 11/2008 | Feodoroff |
| 7,549,179 | B1 | 6/2009 | Saied |
| D598,638 | S | 8/2009 | Graneto, III |
| 7,654,266 | B2 | 2/2010 | Corbitt, Jr. |
| 7,673,754 | B2 | 3/2010 | Wilson, Jr. et al. |
| D622,479 | S | 8/2010 | Herzog |
| D622,934 | S | 9/2010 | Graneto, III |
| 7,841,020 | B2 | 11/2010 | Mayfield et al. |
| 7,971,274 | B2 | 7/2011 | Graneto, III |
| 8,006,836 | B2 | 8/2011 | Trombetta |
| 8,069,495 | B2 | 12/2011 | Kemper |
| 8,162,137 | B2 | 4/2012 | Vellutato, Jr. et al. |
| 8,343,182 | B2 * | 1/2013 | Kirkham ................... 606/203 |
| 8,375,466 | B2 | 2/2013 | Tasezen et al. |
| 8,464,374 | B1 | 6/2013 | Thayer |
| 2002/0095709 | A1 | 7/2002 | Fujikawa et al. |
| 2003/0060831 | A1 | 3/2003 | Bonutti |
| 2003/0121522 | A1 | 7/2003 | Gingles et al. |
| 2004/0019951 | A1 | 2/2004 | Cioffi |
| 2004/0103904 | A1 | 6/2004 | Auerbach et al. |
| 2005/0044608 | A1 | 3/2005 | Ambrose et al. |
| 2005/0145254 | A1 | 7/2005 | Aboul-Hosn et al. |
| 2005/0223468 | A1 | 10/2005 | Hatton |
| 2005/0279366 | A1 | 12/2005 | Adragna |
| 2006/0000002 | A1 | 1/2006 | Bergkvist |
| 2006/0081261 | A1 | 4/2006 | Corbin, Jr. |
| 2006/0117452 | A1 | 6/2006 | Ambrose |
| 2006/0117456 | A1 | 6/2006 | Griesbach |
| 2006/0191541 | A1 | 8/2006 | Aboul-Hosn et al. |
| 2006/0236440 | A1 | 10/2006 | Zahler |
| 2007/0102005 | A1 | 5/2007 | Bonutti |
| 2008/0006279 | A1 | 1/2008 | Bodenham |
| 2008/0023013 | A1 | 1/2008 | Tuke et al. |
| 2008/0047567 | A1 | 2/2008 | Bonutti |
| 2008/0178365 | A1 | 7/2008 | Furgerson et al. |
| 2009/0277460 | A1 | 11/2009 | Carrez et al. |
| 2009/0320177 | A1 | 12/2009 | Lin et al. |
| 2010/0031966 | A1 | 2/2010 | Allen |

(56) References Cited

U.S. PATENT DOCUMENTS

| | | | |
|---|---|---|---|
| 2010/0138975 A1 | 6/2010 | Jordan et al. | |
| 2010/0299805 A1 | 12/2010 | Graneto, III | |
| 2010/0300459 A1* | 12/2010 | Lair | 128/853 |
| 2011/0024485 A1 | 2/2011 | Porowski | |
| 2011/0154554 A1 | 6/2011 | Furlong | |
| 2011/0167534 A1 | 7/2011 | Wong et al. | |
| 2011/0315150 A1* | 12/2011 | Bream, Jr. | 128/855 |
| 2012/0060257 A1 | 3/2012 | Herzog | |
| 2012/0124722 A1 | 5/2012 | Yadav et al. | |
| 2012/0167896 A1 | 7/2012 | Stang et al. | |
| 2012/0312308 A1 | 12/2012 | Allen | |
| 2013/0091616 A1 | 4/2013 | Muche et al. | |
| 2013/0276204 A1 | 10/2013 | Pasko et al. | |
| 2014/0007316 A1 | 1/2014 | Tommarello et al. | |
| 2014/0082816 A1 | 3/2014 | Christopher | |
| 2014/0173814 A1 | 6/2014 | Yadav et al. | |
| 2014/0215681 A1 | 8/2014 | Goodman | |
| 2015/0089712 A1 | 4/2015 | Gamble | |
| 2015/0096099 A1 | 4/2015 | Vanneste | |
| 2015/0113698 A1 | 4/2015 | Gregerson-Brown | |
| 2015/0208741 A1 | 7/2015 | Pasko | |

FOREIGN PATENT DOCUMENTS

| | | |
|---|---|---|
| EP | 0166124 | 1/1986 |
| FR | 2896146 | 7/2007 |
| JP | 2001-510704 | 8/2001 |
| WO | WO-8602258 | 4/1986 |
| WO | WO-99/04721 | 2/1999 |
| WO | WO-01/30258 | 5/2001 |
| WO | WO-2007/083032 | 7/2007 |
| WO | WO-2011/038792 | 4/2011 |

OTHER PUBLICATIONS

Byun, Sung C., "PCT Search Report", PCT No. PCT/US2012/052079; Filed Aug. 23, 2012; Mailed Dec. 26, 2012.
Vanatta, Amy "Non-Final Office Action", U.S. Appl. No. 12/720,360, filed Mar. 9, 2010; Mailed Oct. 11, 2011.
Harris, Raymond E., "Non-Final Office Action", U.S. Appl. No. 12/537,961, filed Aug. 7, 2009; Mailed Nov. 9, 2011.
Vanatta, Amy B., "Notice of Allowance", U.S. Appl. No. 12/720,360, filed Mar. 9, 2012; Mailed Feb. 9, 2012.
Harris, Raymond E., "Final Office Action", U.S. Appl. No. 12/537,961, filed Aug. 7, 2009; Mailed Apr. 11, 2012.
Harris, Raymond E., "NonFinal OA", U.S. Appl. No. 12/537,961, filed Aug. 17, 2009; Mailed Jul. 17, 2012.
Harris, Raymond E., "Final OA", U.S. Appl. No. 12/537,961, filed Aug. 7, 2009; Mailed Nov. 21, 2012.
Chang, Bong Ho "PCT Search Report and Written Opinion", PCT/US2012/054659, filed Sep. 11, 2012; Mailed Feb. 26, 2013.
Haden, Sally C., "NonFinal OA", U.S. Appl. No. 13/276,232, filed Oct. 18, 2011; Mailed Apr. 8, 2013.
Haden, Sally C., "Final OA", U.S. Appl. No. 13/276,232, filed Oct. 18, 2011; Mailed Jul. 17, 2013.
Haden, Sally C., "NonFinal OA", U.S. Appl. No. 13/925,617, filed Jun. 24, 2013; Mailed Aug. 14, 2013.
Hicks, Victoria "NonFinal OA", U.S. Appl. No. 13/229,743, filed Sep. 11, 2011; Mailed Feb. 10, 2014.
Hicks, Victoria "NonFinal OA", U.S. Appl. No. 13/589,640, filed Aug. 20, 2012; Mailed Jun. 13, 2014.
Hicks, Victoria "Final OA", U.S. Appl. No. 13/229,743, filed Sep. 11, 2011; Mailed Aug. 7, 2014.
Hicks, Victoria "Final OA", U.S. Appl. No. 13/589,640, filed Aug. 20, 2012; Mailed Jan. 2, 2015.
"Extended European Search Report", EP Application No. 12790027.2; PCT/US2012/032122; Mailed Jan. 5, 2015.
Gimenez Burgos, R "Extended European Search Report", EP 12829356.0-1659/2747696; PCT/US2012052079; Reference No. SJG/P131402EP00; Mailed Feb. 16, 2015.
Gimenez Burgos, R "Extended European Search Report", App No. 12834067.6-1659/2747697; Reference No. SJG/P131778EP00.
"First Office Action", CN Application No. 201280046346.4; Filed Sep. 11, 2012; Mailed Aug. 26, 2015.
Wu, Jocelyn Mary "NonFinal OA", U.S. Appl. No. 14/086,798, filed Nov. 21, 2013; Mailed Sep. 24, 2015.
Reed, Richard "First Examination Report", Australian Application No. 2012259325; Exam Request Date Mar. 5, 2015; Reference No. 35210639/GCP; Mailed Nov. 30, 2015.
"Final OA", U.S. Appl. No. 14/086,798, filed Nov. 21, 2013; Mailed Feb. 1, 2016.
"Office Action", Canadian Office Action for Canadian Patent No. 2,674,951 dated May 4, 2011 (3 pages).
European Search Report for European Applicafion No. 09167307.9 dated Oct. 11, 2010 (5 pages).
3M Technical Information Sheet, Product No. 1521, Feb. 2007 (2 pages).
3M Product Clinical Data Summary for No. 1521, 3M Plastic Medical Tape, Jan. 1996 (2 pages).
Medical Single Coated Film Tapes Selection Guide—Polyolefin & Vinyl, Nov. 1996 (3 pages).
Description and Photographs of D-09875-001 Snap Drape (as of Oct. 6, 2008) (1 page).
Description and Photographs of 75-1040 Fenestrated Snap Drape (as of Oct. 6, 2008) (1 page).
Description and Photographs of Perforated Drapes (as of Oct. 6, 2008) (2 pages).
Description and Photographs of a Perforated Drape With Tear Line (as of Oct. 6, 2008) (1 page).
"Office ACtion", Chinese App No. 201280046346.4; Mailed Apr. 21, 2016.
"Office Action", JP Application No. 2014-531859; Mailed May 2, 2016.
"Notice of Allowance", Japanese App No. 2015-531859; Mailed Nov. 24, 2016.
"Office Action", Australian Patent Application 2012304800; Mailed Nov. 22, 2016.
Pandika, Kylie "Examination Report", Australian Patent Application No. 2012312845; Filed Sep. 23, 2011; Mailed Nov. 1, 2016.
"Office Action", Chinese App No. 201280046346.4; Mailed Oct. 21, 2016.
"Medline Catalog", Full BodyDrapes by Halyard Health; Medline Catalog; http://www.medline.com/catalog/catalog.jsp; Unknown Publication date but believed to be prior to present application filed.
"Medline Catalog", K-C100 Mayo Stand Covers by Halyard Health; Medline Catalog; http://www.medline.com/catalog/catalog.jsp; Unknown Publication date but believed to be prior to present application filed.
"Medline Catalog", Midline Cath Picc Kits by Medikmark; Medline Catalog; http://www.medline.com/catalog/catalog.jsp; Unknown Publication date but believed to be prior to present application filed.
"Medline Catalog", Picc Full Body Coverage Pack by Halyard Health; Medline Catalog; http://www.medline.com/catalog/catalog.jsp; Unknown Publication date but believed to be prior to present application filed.

* cited by examiner

US 9,820,751 B2

SURGICAL DRAPE CONFIGURED FOR PERIPHERALLY INSERTED CENTRAL CATHETER PROCEDURES

BACKGROUND

Technical Field

This invention relates generally to medical gowns, and more particularly to a gown configured to facilitate prevention of infection and other complications during medical procedures.

Background Art

Healthcare facilities are increasingly concerned about the occurrence of "secondary infection" occurring during medical and surgical procedures. As a result, more attention is being turned to establishment and maintenance of sterile fields about patients and procedure sites. For example, some healthcare facilities request medical professionals to check and double check certain conditions, such as whether a proper sterile field has been established or whether a proper sterile field can be maintained. Despite these warnings, it can some times be difficult to remember to check and double check each condition. Further, it can be difficult to maintain sterile fields with some currently existing equipment.

It would be advantageous to have equipment configured to reduce contamination of sterile fields during medical procedures.

Figure 1:
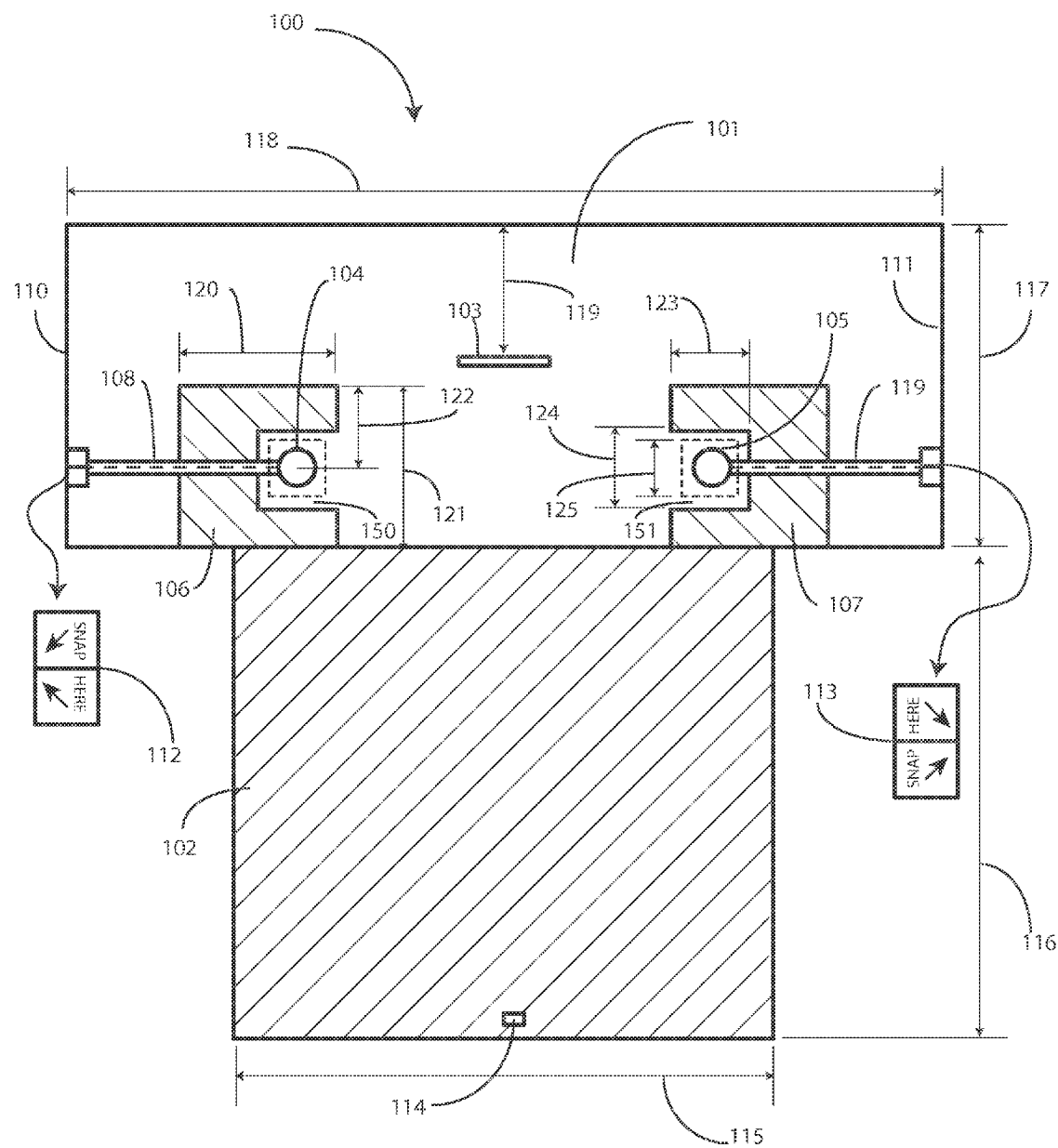
FIG. 1 illustrates a non-patient side of one embodiment of a medical drape configured in accordance with one or more embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EMBODIMENTS OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

A central catheter is a catheter that is placed into a large vein through which medical professionals may repeatedly deliver fluids or medications to a patient. Central catheters can also be used to withdraw fluids, such as blood, for testing. Central catheters can be inserted into various parts of the patient, but are generally inserted in veins in the neck. Central catheters inserted into arms are known as "peripherally" inserted central catheters. Peripherally inserted central catheters are frequently placed in a patient's arm to allow prolonged intravenous access, such as for extended antibiotic treatment, chemotherapy, and so forth. Peripherally inserted central catheters are frequently left in place in the patient's arm for periods ranging from six weeks to one year.

Catheter insertion procedures, including peripherally inserted central catheter procedures, are generally performed bedside by a medical professional who specializes in insertion. The medical professional is frequently a specially trained nurse. One exception to bedside insertion occurs during radiology procedures, where the catheter is guided and inserted by a doctor.

Regardless of who inserts the catheter, or where it is inserted, bloodstream infection is a concern. It will be readily understood that insertion of a semi-permanent object into a patient's vein has associated therewith a risk that bacteria or other microbes will be introduced into the bloodstream during central catheter and peripherally inserted central catheter insertion procedures. Studies have shown that such infections can be a source of death. The largest percentage of these infections occurs at the time of catheter insertion.

To combat this, some health care providers have begun to issue procedure requirements that are similar to those used in surgery. For example, a catheter insertion specialist must don hair covering, a mask, gloves, foot coverings, and a full-body sterile surgical gown, just as if they were entering an operating room. Such procedures also require the patient to be covered by a conventional medical drape. Such procedures attempt to ensure that a maximum barrier environment is established prior to the insertion of central lines.

While the procedures are beneficial, they are insufficient for preventing bloodstream infections during central line procedures for two reasons: First, it is frequently the case that medical personnel performing line placement are unfamiliar with "surgical" practices and aseptic techniques used during operations. Said differently, central catheter insertion personnel generally do not work in the operating room, and are therefore frequently unacquainted with operating room procedures. Accordingly, such personnel therefore frequently lack understanding of certain techniques, including correct steps in tying tourniquets and when to drape the patient. These deficiencies can cause breaks in aseptic technique. For example, tying a tourniquet too soon could cause damage to the patient. Nonetheless, in catheter insertion, procedures frequently suggest the tourniquet be tied before the sterile field is created, which is still before the medical personnel dons the equipment listed above. Thus, some medical personnel may be tempted to apply tourniquets required in central line insertion procedures too soon.

A second problem is that central catheters and peripherally inserted central catheters are frequently inserted by a single person, not a team. Consequently, the insertion personnel must juggle many items and perform many complex steps to ensure sterile fields using conventional equipment and drapes. Application of prior art drapes requires at least two people to prevent compromise of the sterile field. When one person attempts to apply a drape in a catheter insertion procedure, he or she risks compromise of any sterile field that may be required for the procedure.

Embodiments of the present invention work to solve both problems by providing a full body procedural drape that is specifically configured for central catheter insertions. While peripherally inserted central catheters will be used below as an illustrative application, it will be clear to those of ordinary skill in the art having the benefit of this disclosure that the invention is not so limited. Minor modification of drapes described herein, such as slight movement and relocation of the components described below, will permit drapes configured in accordance with embodiments of the invention to be readily used for a wide variety of central line or catheterization procedures.

Advantages offered by the embodiments of the invention, as compared to prior art designs, include that the drapes described below help to address claustrophobic or enclosed feelings of the patient under the drape, help medical personnel more easily apply, use, and remove tourniquets, help ensure proper aseptic techniques, and help in removal of the drape without compromising the integrity of the catheter. An additional advantage offered by embodiments of the invention is that they can be applied by a single person without compromising the sterile field about the patient.

Embodiments described below provide a medical drape, suitable for use in peripherally inserted central catheter and other procedures, that work as full-body drapes and that are easy for one person to open and apply. Additionally, medical drapes described below can be universally configured for use with the right or left arm. As patients are generally awake for peripherally inserted central catheter procedures, one or more embodiments described below provide a full, clear panel in the top portion covering the patient's face so the patient does not feel "enclosed." This is in contrast to conventional drapes, which are fully opaque. In one embodiment, to provide additional patient comfort, a tenting bar is incorporated into the clear panel. The tenting bar allows the medical personnel to fashion the bar so as to retain the clear panel away from portions of the patient's face, thereby allowing easier breathing and reduced stress.

The clear panel provides additional benefits as well. For instance, the clear panel makes it possible for medical personnel to see the patients arm for better application and removal of tourniquets and for better insertion of the central line. In one embodiment, the medical drape is configured with a T-shaped cross section to facilitate bedside line insertion. A table can be placed bedside beneath the horizontal portion of the T-shaped cross section. While most prior art drapes would result in contamination of the sterile field after the drape is placed on the patient, the T-shape ensures that the sterile field is maintain.

Some embodiments include integral tourniquets that prevent medical personnel from "fishing" for a tourniquet that is beneath an opaque drape, as is the case in prior art designs. The tourniquets can include closure devices on the patient side of the drape, such as snap-locking device or buckle-type closure.

In one or more embodiments, the medical drape includes a tool-less removal feature that allows drape to be easily removed at the end of the procedure. The tool-less removal feature allows the drape to "break away" from the insertion site, thereby preventing accidental tugging or pulling of the remaining line.

Figure 2:
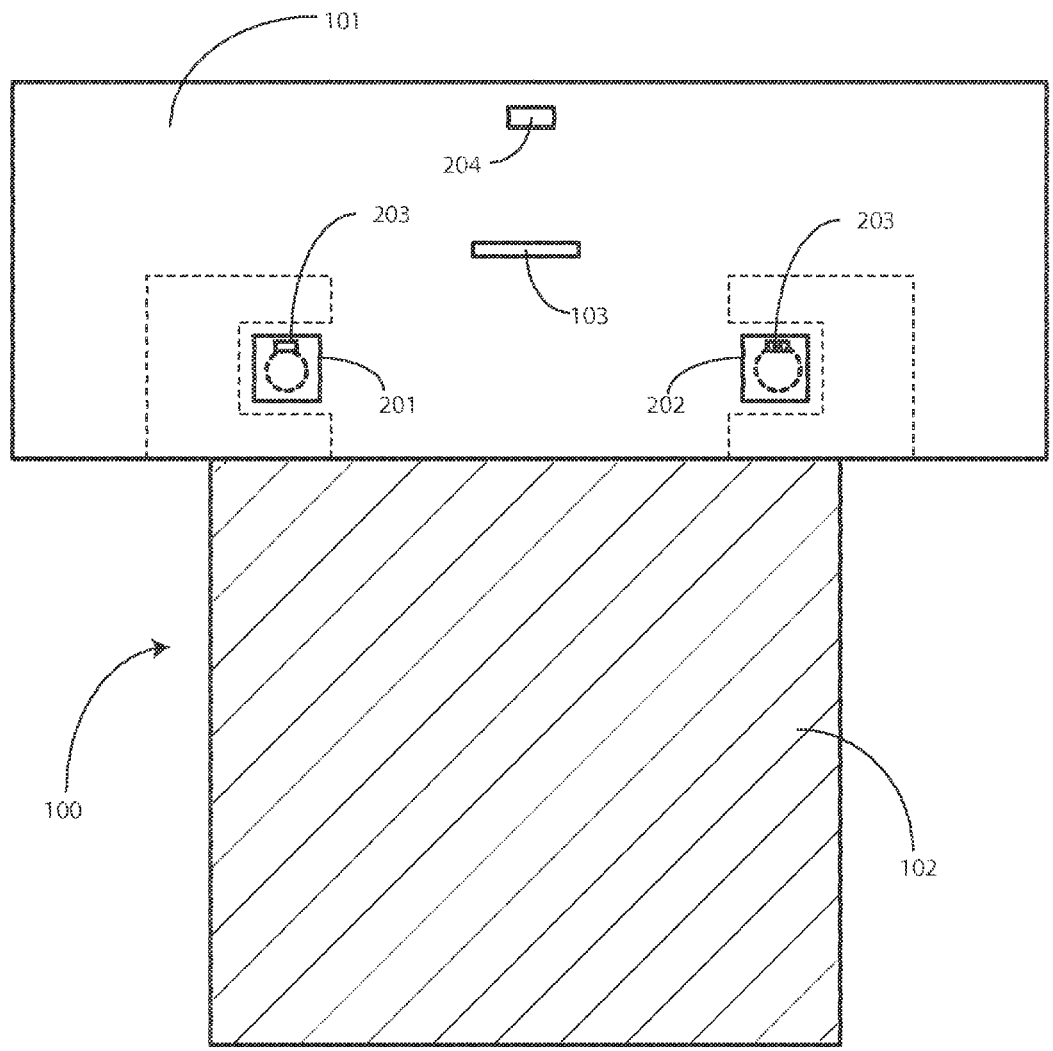
FIG. 2 illustrates a patient side of one embodiment of a medical drape configured in accordance with one or more embodiments of the invention.

Turning now to FIGS. 1 and 2, illustrated therein is one embodiment of a medical drape 100 suitable for peripherally inserted central catheter and other catheterization procedures. FIG. 1 illustrates a plan view of the "non-patient" or "medical personnel" side, while FIG. 2 illustrates a plan view of the "patient side." The side of FIG. 2 is referred to as the "patient side" because it is the side that will contact the patient when the medical drape 100 is used in a catheter insertion procedure. The medical drape 100 is bisected because it is divided into a first portion that is, in one embodiment, transparent, and a second portion that is, in one embodiment, opaque.

The illustrative medical drape 100 of FIG. 1 has a T-shape when viewed in plan view, with an upper portion 101 being wider than the lower portion 102. In one embodiment, the upper portion 101 is configured to be wide enough to cover at least the arms and head of a patient. The lower portion can be configured to cover the torso portions of the patient. Generally, these torso portions will be at least inferior to the abdominal portion of the patient. Illustrating by example, the upper portion 101 can be configured for positioning over a brachial portion of a patient, a cubital portion of the patient, an antibrachial portion of the patient, or combinations thereof, while the lower portion 102 can be configured to cover patient portions inferior thereto.

In one or more embodiments, the upper portion 101 and lower portion 102 are manufactured from different materials. In one embodiment well suited for peripherally inserted central catheters, the upper portion 101 is pellucid while the lower portion 102 is opaque. In another embodiment, the upper portion 101 is transparent, while the bottom portion is any of non-transparent, opaque, or non-pellucid. For example, in one embodiment the upper portion can be manufactured from clear 0.05 mm polyethylene sheeting. It should be noted that other clear, flexible materials may be used in place of polyethylene. Similarly, the lower portion 102 can be manufactured from 45 g spunbond-meltblown-spunbond material. Other materials can be used for the lower portion 102, including, for example, various woven, non-woven, hydroentangled materials, and/or combinations thereof, absorbent Airlaid, spunlace, blends of polyester, polypropylene, polyethylene, urethane, and/or combinations thereof, using various methods, including a spunbond metblown spundbond (SMS) method, a spunbond metblown metblown spundbond method (SMMS), and a spunbond metblown metblown spundbond method (SMMMS). Suppliers of such materials include Cardinal Health in Dublin, Ohio, Kimberly Clark in Neena, Wis., Molnycke Health Care in Newtown, Pa., and Precept Medical Products, Inc., in Arden, N.C. These materials and methods are illustrative only, as others will be readily apparent to those of ordinary skill in the art having the benefit of this disclosure. For example, one or more antimicrobial layers can be added to further enhance antimicrobial protection. Additionally, the material can optionally include and water resistant lining that prevents the passage of fluids through the material.

Configuring the upper portion 101 to be pellucid or transparent offers several advantages over prior art drapes. First, it allows the patient to see what is going on during the procedure. This results in a patient that feels less claustrophobic and more at ease. Second, it allows the insertion personnel to fully see the insertion site. Third, when tourniquets are involved, as is the case with peripherally inserted central catheters, the pellucid nature of the upper portion allows the insertion personnel to quickly find and use the tourniquet. Fourth, where additional procedures such as ultrasound imaging are required, predetermined minimum areas 150,151 of the upper portion 101 permit an ultrasound technician or other medical services provider to see a patient's limbs through these predetermined minimum areas 150,151. Said differently, in one embodiment the predetermined minimum areas 150,151 are sufficient for a patient's limb disposed beneath the transparent portion to be visible from above the transparent portion. Configuring the lower portion 102 to be opaque allows portions of the patient not involved in the procedure to be covered, thereby maintaining patient dignity.

In one embodiment, the upper portion 101 includes a tenting bar 103. In one embodiment, the tenting bar 103 is centrally disposed along the upper portion 101, although other applications may suggest placing the tenting bar 103 elsewhere. The tenting bar 103 can be attached to the upper portion, such as by adhesive or other means. Alternatively, the tenting bar 103 can be integrated into the upper portion 101, such as with a molding or integration process.

The tenting bar 103 is included to position at least some of the upper portion 101 away or apart from the patient's face when the medical drape 100 is disposed atop the patient (along an anterior portion of the patient). This will be shown in more detail in the discussion of FIG. 6.

In one embodiment, the tenting bar 103 is manufactured from a flexible or bendable material. Soft aluminum, copper, alloy, or other materials can be used to form the tenting bar 103. When the tenting bar 103 is configured from a bendable material, medical personnel can tailor the tenting bar 103 for maximum separation between the patient's face and the upper portion 101, or for maximum patient comfort, once the medical drape 100 has been placed over the patient.

In one or more embodiments, the medical drape 100 has one or more apertures 104,105 configured for placement over a central catheter insertion site. The apertures 104,105 can be configured as fenestrations in the medical drape 100 that define openings or apertures in one or more embodiments. The illustrative embodiment of FIG. 1 includes a first aperture 104 and a second aperture 105, which provide a "universal" drape that can be used for catheter insertion in either a patient's right or left arm. It will be clear to those having benefit of this disclosure that customized "right handed" or "left handed" drapes could be configured with only one aperture. Similarly, expanded usage drapes could be configured with three or more apertures. For example, one drape could have the first aperture 104, the second aperture 105, and a third aperture (not shown) configured for placement over a patient's neck. The apertures 104,105, in one embodiment, are configured to allow a peripherally inserted central catheter to be inserted through one of the apertures 104,105 when the medical drape 100 is disposed atop the patient. The apertures 104,105 or fenestrations could be configured to accommodate other medical procedures as well.

In one or more embodiments, an absorptive element 106,107 is disposed about the apertures 104,105. In the illustrative embodiment of FIG. 1, the absorptive elements 106,107 have a substantially U-shape and are placed on the exterior sides of the upper portion 101 relative to the apertures 104,105. The absorptive elements 106,107 can be gauze-like, a non-woven absorbent material, or other absorptive material configured to absorb fluids, such as blood, that may become present during a catheterization procedure.

In one embodiment, the absorptive elements 106,107 are arranged such that a predetermined minimum area 150,151 of the upper portion 101, which in this embodiment is transparent, is disposed between the absorptive elements 106,107 and the apertures 104,105 or fenestrations. In this illustrative embodiment, the predetermined minimum areas 150,151 are one and a half inch wide strips that pass about the apertures 104,105. Such minimum areas of transparent material are helpful in a variety of applications. For example, it is sometimes the case that an ultrasound procedure is used during a catheterization procedure. When this is the case, an ultrasound technician may need to see the patient's limb through the upper portion 101 of the drape 100. If the absorptive elements 106,107 extend to the apertures 104,105, this is not possible. However, when the predetermined minimum areas 150,151 are included, the patient's limb disposed beneath the upper portion 101 becomes visible from above the upper portion 101.

In one or more embodiments, to keep the apertures 104,105 closed until needed, releasable coverings 201,202 may be attached over each aperture 104,105. In this illustrative embodiment, the releasable coverings 201,202 comprise conventional medical release paper affixed to the patient side of the medical drape 100. One suitable means for affixing the releasable coverings 201,202 to the medical drape is with sections 203 of adhesive tape. The adhesive tape can be a single-coated polyethylene medical tape, such as a medical tape manufactured by 3M (St. Paul, Minn.) as product number 1521. The 3M Medical Tape 1521 is a single-coated tape having a matte finish which includes a transparent polyethylene and is coated with a hypoallergenic, pressure sensitive acrylate adhesive and includes a liner that is silicone treated and is polyethylene coated on one side only along with a bleached Kraft paper release liner. The 3M medical tape has a tape caliper of 6.4 mil (0.16 mm) of polyethylene film tape, a backing of 5.0 mil (0.13 mm) translucent polyethylene film, an acrylate adhesive (designed for medical/surgical use), and a release liner of 83 lb poly-coated Kraft paper, with silicone on one side (6 mils/ 0.15 mm). The adhesion to steel of the 3M Medical Tape 1521 is 21 ounces/inch width (0.6 kg/25 mm width). Other suitable medical tapes manufactured by 3M and/or other manufacturers may be used as well. For example, where the adhesive tape is double-sided, the tape can also be used to temporarily attach the upper portion 101 to the patient. This ensures that the aperture 105 remains over the insertion site without requiring the insertion specialist to continually hold the upper portion 101 in place.

In one or more embodiments, to make removal of the medical drape 100 easier, a tool-less removal feature 108, 109 can be incorporated into the upper portion 101. One example of a tool-less removal feature is described in commonly assigned, co-pending patent application U.S. Ser. No. 12/188,931, filed Aug. 8, 2008, entitled "Zip Strip Draping System and Methods of Manufacturing Same," Fred L. Allen, inventor, which is incorporated herein by reference.

In one embodiment, the tool-less removal feature 108, 109, which is described in more detail with reference to FIG. 3 below, includes a drape cut, adhesive tape strip, and score line, each of which extends from an edge 110,111 of the upper portion 101 to a corresponding aperture 104,105. In the illustrative embodiment of FIGS. 1 and 2, the tool-less removal feature 108,109 extends from an edge of the drape 100, across the absorptive elements 106,107, across the predetermined minimum areas 150,151 of transparent material, and to the apertures 104,105. Said differently, the drape cut, adhesive tape strip, and score line can begin at an edge, e.g., edge 110, and passes along the upper portion 101 to an aperture, e.g., aperture 104.

The adhesive tape strip is positioned along the length of the drape cut to overlap a portion of the drape material on both sides of the drape cut to initially secure the adjoining drape cut sides together. The score line permits easy tearing of the adhesive tape strip to open the drape cut. Usage of the tool-less removal features 108,109 allow the upper portion 101 to be removed without disturbing a peripherally inserted central catheter that has been placed through one of the apertures 104,105.

In one or more embodiments, to show medical personnel where to begin opening the tool-less removal features 108, 109, indicators 112,113, which are shown in a blown-up view in FIG. 1, can be disposed at edges 110,111 of the upper portion 101. Said differently, indicators 112,113 can be included to indicate the starting point of each tool-less removal feature 108,109. The indicators 112,113, which may include instructional indicia such as the words "Tear Here" or "Snap Here." Accordingly, medical personnel knows to grasp and pull apart the indicators 112,113 to tear apart the adhesive tape strip along the score line to "peel" the upper portion 101 about the inserted central line. Other indicators 114,204 can be included as well, such as indicators alerting medical personnel which end is the "head" (indicator 204) and "foot" (indicator 114), respectively.

Illustrative dimensions now are provided to further describe one embodiment suitable for use in peripherally inserted central catheter applications. It will be clear to those of ordinary skill in the art having the benefit of this disclosure that these dimensions are examples only, provided to present a clearer image of one embodiment, and can readily be modified based upon application or customer demand.

In one embodiment, the lower portion 102 has a width 115 of sixty-four inches, plus or minus one inch. In one embodiment, the lower portion 102 has a length of sixty-three inches, plus or minus one inch. In one embodiment, the upper portion 101 has a length of forty-one inches, plus or minus one inch. In one embodiment, the upper portion 101 has a width 118 of one hundred and twelve inches, plus or minus one inch. In one embodiment, the tenting bar 103 is about three-quarters of an inch wide and about eleven inches long. The tenting bar in this embodiment is centrally disposed along the width 118 of the upper portion 101, and is disposed a distance 119 of about seventeen inches from the top of the upper portion 101.

In one embodiment, the width 120 of the absorptive elements 106,107 is about twenty inches. In one embodiment, the length 121 of the absorptive elements 106,107 is about twenty inches. In one embodiment, the absorptive elements 106,107 extend a distance 122 of about ten inches from the center of the apertures 104,105. In one embodiment, the "arms" of the U-shape of the absorptive elements 106,107 have a width 123 of about ten inches. In one embodiment, the center of the U-shape of the absorptive elements 106,107 is a distance 124 of about ten inches. In one embodiment, the width 125 of the releasable coverings 201,202 is about seven inches.

Figure 3:
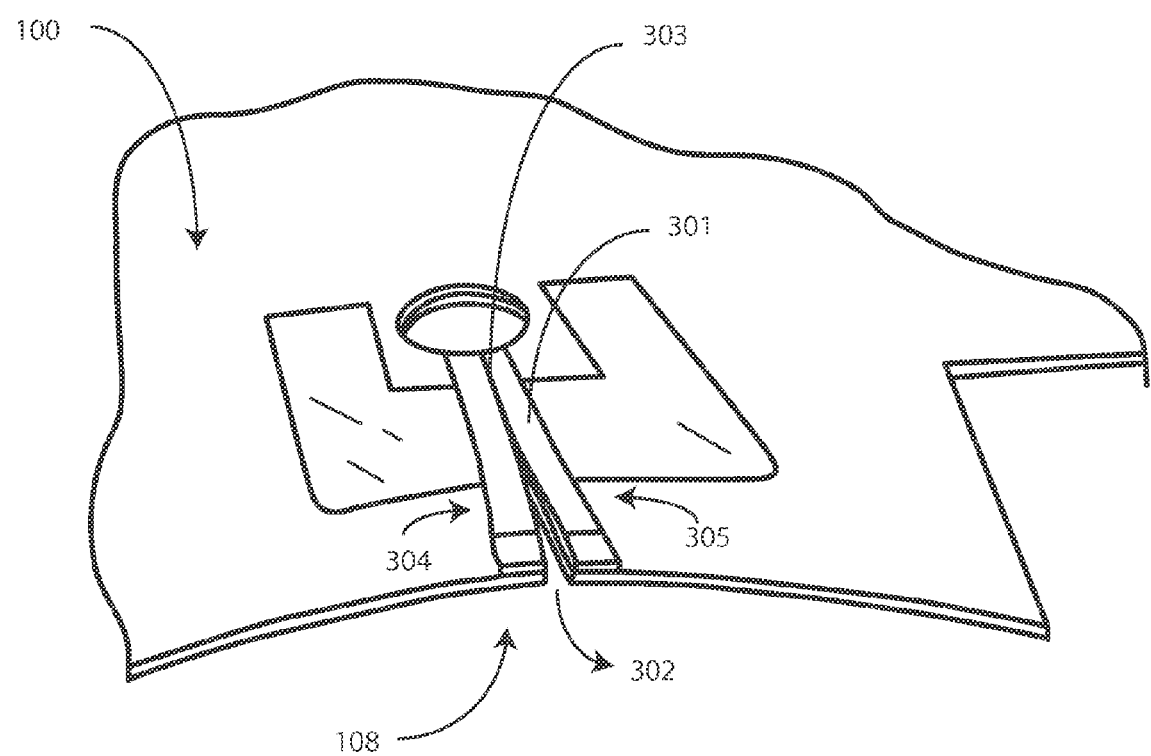
FIG. 3 illustrates one illustrative tool-less removal feature suitable for use with one or more medical drapes configured in accordance with one or more embodiments of the invention.

Turning now to FIG. 3, one of the tool-less removal features 108 is shown in more detail. As noted above, in one embodiment the tool-less removal feature 108 includes an adhesive tape strip 301, a drape cut 302, and a score line 303. The adhesive tape strip 301 generally includes a first strip side 304 and a second strip side 305, which are connected along the score line 303. The score line 303 can be formed by partially severing the adhesive tape strip 301 along its length. Thus, the first strip side 304 can be easily separated from the second strip side 305 to open the drape cut 302. In addition to securing the drape cut 302, the adhesive tape strip 301 seals the drape cut 302 to prevent any violation of a sterile field formed on the patient side of the medical drape 100.

Figure 4:
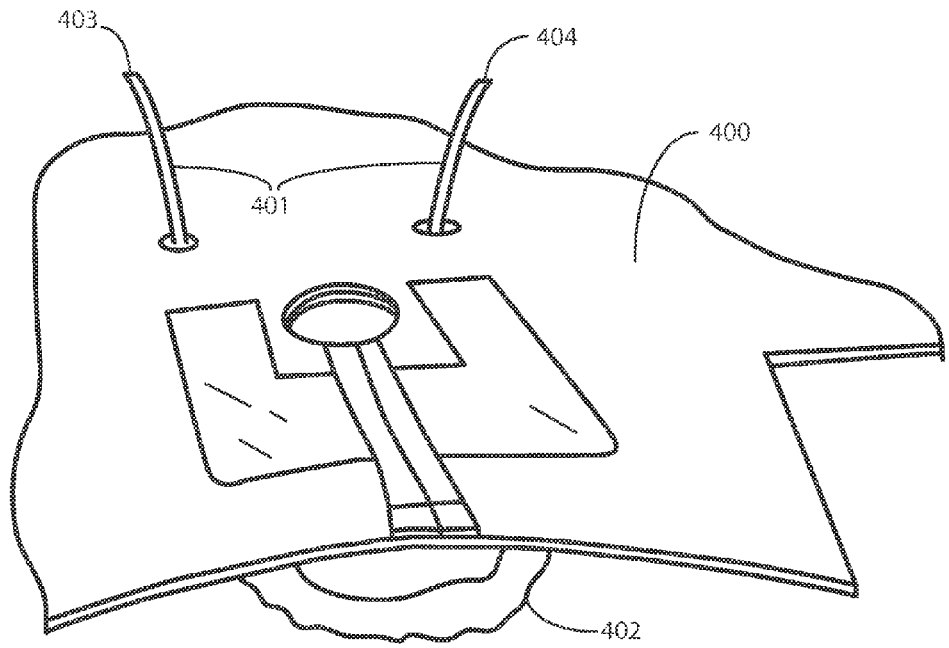
FIGS. 4 and 5 illustrate a perspective and side view, respectively, of one illustrative embedded tourniquet suitable, but optional, for use with one or more drapes configured in accordance with embodiments of the invention.
Figure 5:
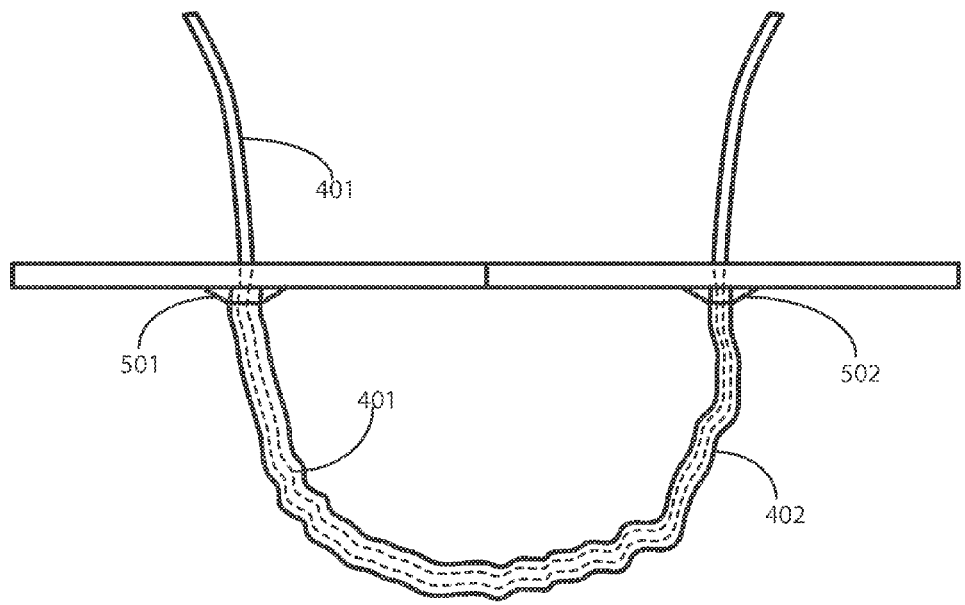

Turning now to FIGS. 4 and 5, illustrated therein is an alternate feature that may optionally be included in one or more medical drapes configured in accordance with embodiments of the invention. As noted above, peripherally inserted central catheter procedures require tourniquets. Prior art drapes required medical personnel to fish around under an opaque drape to blindly place, apply, and release a tourniquet. FIGS. 4 and 5 illustrate a more advantageous means of accomplishing this task.

More specifically, FIGS. 4 and 5 illustrate a tourniquet 401 integrated with a layer 400 of the drape material. The illustrative tourniquet 401 passes through a sleeve 402 that is disposed on the patient side of the layer 400 of drape material. Ends 403,404 of the tourniquet 401 extend outwardly on the non-patient side so as to be accessible by medical personnel.

The sleeve 402 can be integrated into the layer 400 of drape material by sealing features 501,502 that prevent any access to the tourniquet 401 from the patient side of the drape. For example, where the layer 400 of drape material is the polyethylene of the upper portion (101) described above, the sleeve 402 can also be made from polyethylene as well, with the sealing features 501,502 being made from thermoplastic that is integrally formed, such as by ultrasonic sealing, with the polyethylene to prevent moisture or other materials from reaching the tourniquet 401. This preserves the sterile field on the patient side, while providing access to the tourniquet 401 on the non-patient side.

When included in a medical drape, the patient can slip their arm through the sleeve 402 when being covered with the drape. The tourniquet 401 can remain loose until needed. The tourniquet 401 can further be easily applied and released, as needed, without the fishing and uncertainty associated with prior art systems.

Figure 6:
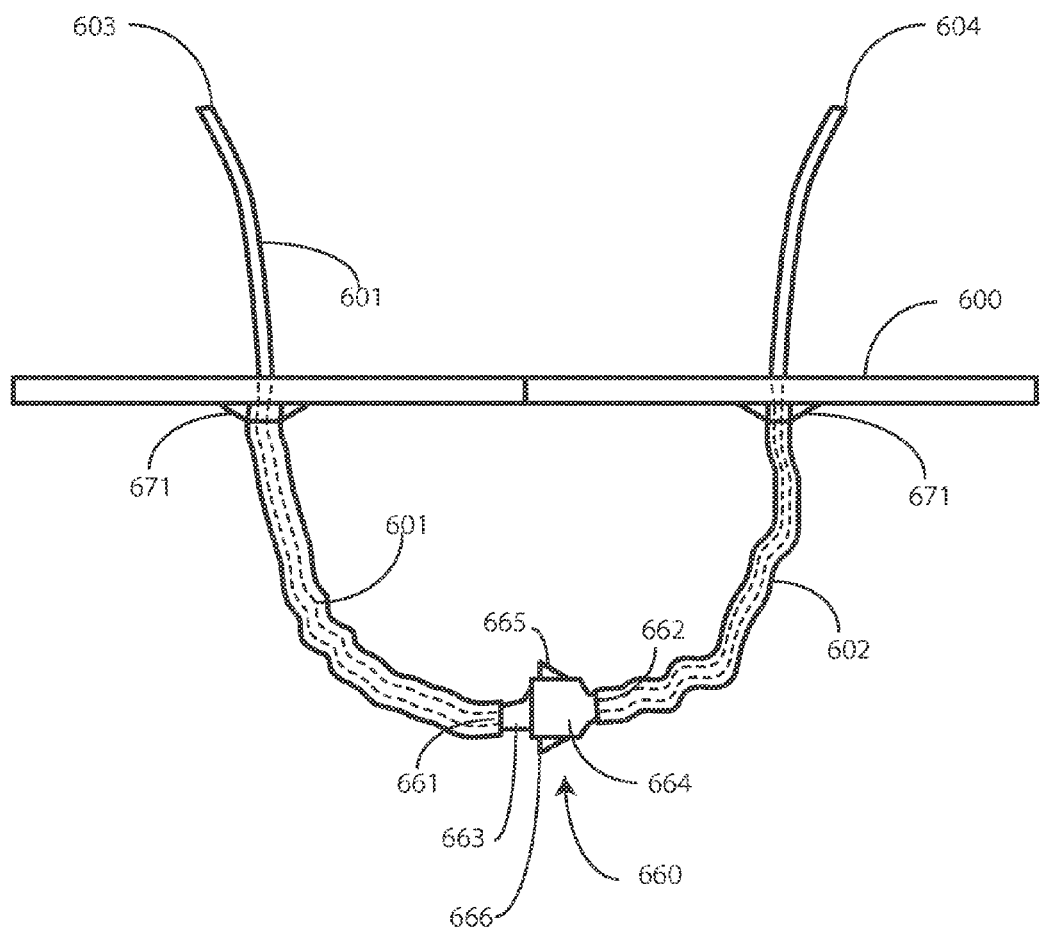
FIG. 6 illustrates another illustrative embedded tourniquet configured for optional use with one or more drapes in accordance with embodiments of the invention.

Turning now to FIG. 6, illustrated therein is another alternate feature that may optionally be included in one or more medical drapes configured in accordance with embodiments of the invention, where those drapes include integrated tourniquets 601. As will be described in more detail below, one advantage of drapes configured in accordance with the present disclosure is that they can be easily used and removed by a single person. This is in contrast to prior art drapes, where two people were generally required for application to preserve the sterile field. The drape 600 of FIG. 6 makes the tourniquet process even simpler for a single health care services provider to use by including a coupler 660 that bisects the tourniquet 601. Accordingly, rather than having to fold the patient's arm back and slide it through a loop, the health care services provider is able to simply snap the coupler 660 about the patient's limb when the drape 600 is being unfolded.

In the illustrative embodiment of FIG. 6, the tourniquet 601 integrated with a layer of the drape 600, which in one embodiment is the transparent or pellucid portion. The illustrative tourniquet 601 passes through a sleeve 602 that is disposed on the patient side of the drape 600. The coupler 660, which is disposed on the patient side of the drape 600, bisects the sleeve 602. A first end 661 of the sleeve 602 is attached to a first part 663 of the coupler 660, while a second end 662 of the sleeve 602 is attached to a second part 664 of the coupler 660. In one embodiment, the coupler 660 comprises a snap-locking device with snap features 665,664 extending from the second part of the coupler 660. Other types of couplers 660 could also be used, including hook and latch couplers, snap couplers, buckle couplers, and so forth. Ends 603,604 of the tourniquet 601 extend outwardly on the non-patient side so as to be accessible by medical personnel. The sleeve 602 can be integrated into the drape 600 by sealing features 671,672 that prevent any access to the tourniquet 601 from the patient side of the drape.

Figure 7:
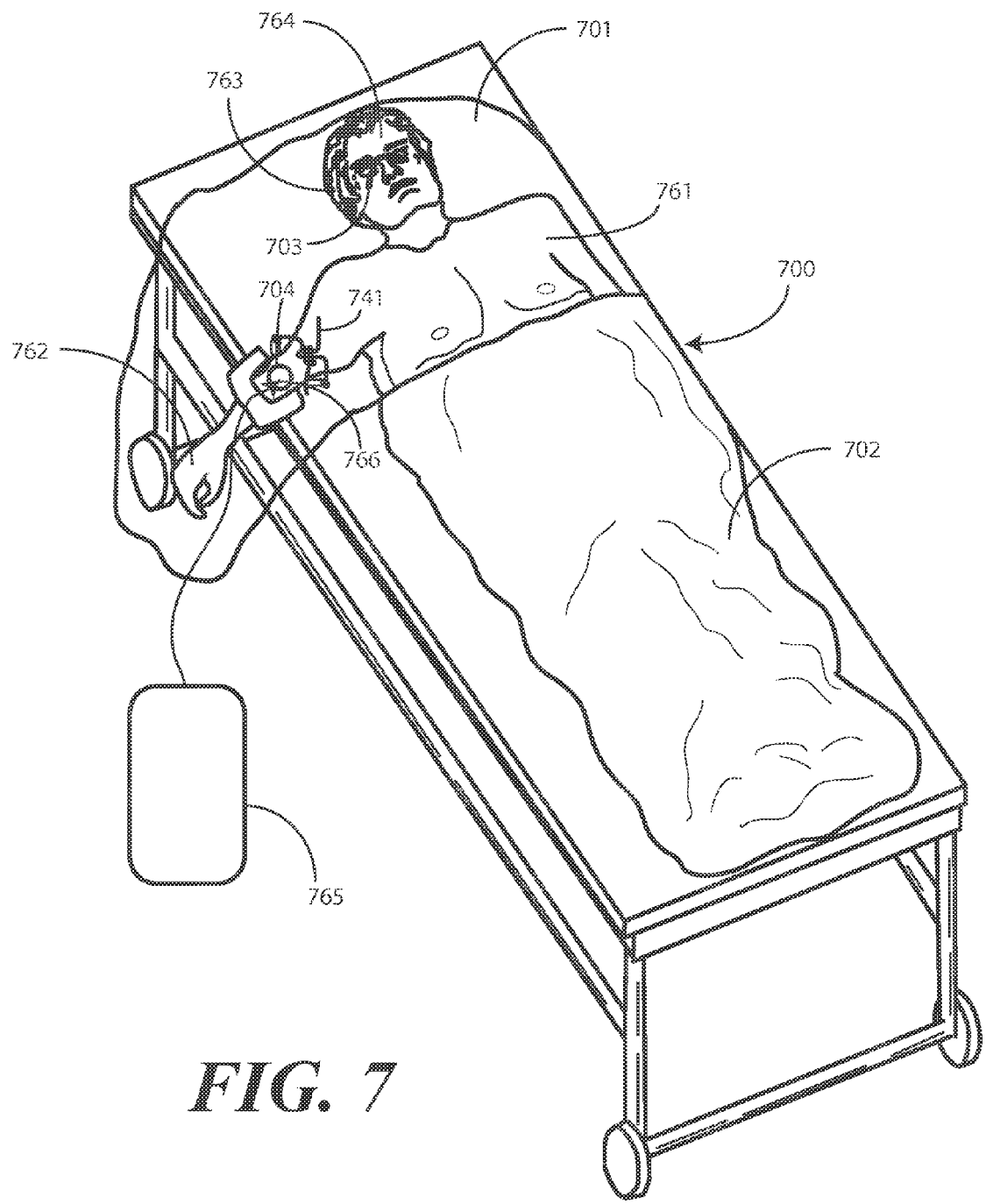
FIG. 7 illustrates one embodiment of a medical drape configured in accordance with embodiments of the invention being used during a peripherally inserted central catheter procedure.

Turning to FIG. 7, a patient 761 is shown being covered with a medical drape 700 configured in accordance with embodiments of the invention. The first portion 701 of the medical drape 700 is placed over the arms 762 and head 763 of the patient 761, with the second portion 702 of the medical drape 700 covering the torso portions of the patient 761. The tenting bar 703 has been formed to keep at least some of the upper portion 701 away from the patient's face 764.

An aperture 704, which is configured in this illustrative embodiment as a fenestration through which a health care services provider has entered, has been placed over a peripherally inserted central catheter insertion site 766. Accordingly, a peripherally inserted center catheter 765 can be inserted through the aperture 704.

This particular medical drape 700 includes an integrated tourniquet 741, which has been tied in this illustration by accessing ends of the tourniquet 741 from the patient side of the medical drape 700. There is no risk of compromising the sterile field because the tourniquet 741 passes through a sleeve that is integrated with the first portion 701 on the patient side of the medical drape 700.

Figure 8:
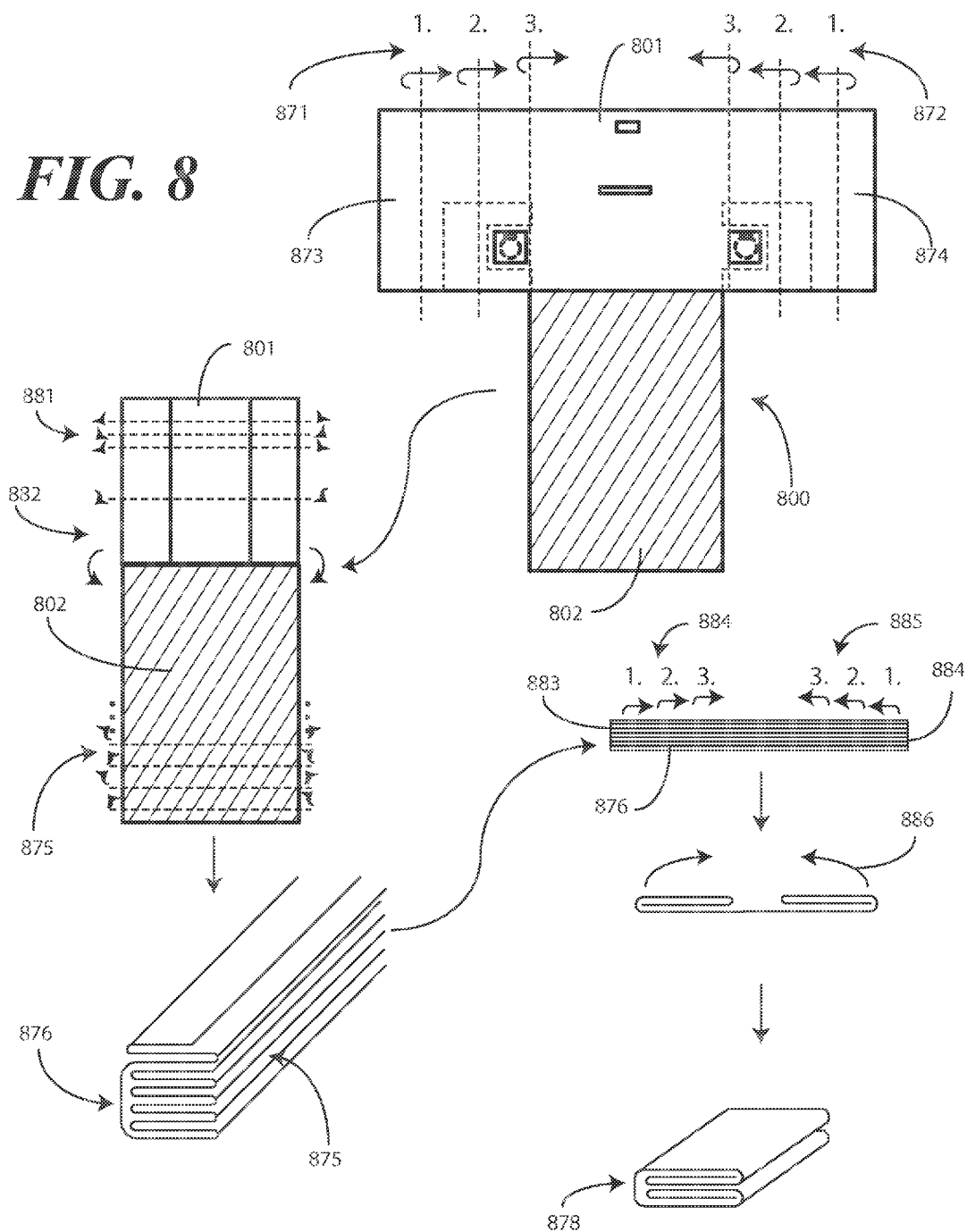
FIG. 8 illustrates one method of folding a medical drape in accordance with embodiments of the invention.

Turning now to FIG. 8, illustrated therein is a method for folding medical drapes 800 configured in accordance with embodiments of the invention. The folding method of FIG. 8 facilitates quick, easy, and accurate placement of the medical drape 800 atop a patient prior to a procedure. Moreover, the folding method of FIG. 8 allows a single person to apply the drape 800 during a catheterization procedure without compromising an established sterile field required to perform the procedure.

The method of FIG. 8 results in the medical drape 800 being folded in multiple ways: First, a first extended side 873 of the medical drape 800 is folded toward the center of the upper portion 801 of the medical drape 800 with a first rolling fold 871. The first rolling fold 871 extends towards and over a center portion of the upper portion 801. A second rolling fold 872 folds a second extended side 874 of the upper portion 801 towards and over the center of the first portion 701.

Next, the lower portion 801 of the medical drape 800 is folded towards the upper portion 802 with an accordion fold 875. The upper portion 802 is folded with two folds: an enclosing fold 882 and a second accordion fold 881. The enclosing fold 882 will wrap about the accordion fold 875 of the second portion as shown in partially complete pre-folded drape assembly 876. An extension extending from the enclosing fold 882 is folded in the second accordion fold, as shown in the pre-folded drape assembly 876. The enclosing fold 882 passes above at least some of the first portion 801 and its accordion fold 875.

From this point, ends 883,884 of the pre-folded drape assembly 876 are folded towards the center of the pre-folded drape assembly 876 with additional rolling folds 884,885. A book fold 886 can then be applied to form folded drape 878. The steps shown in FIG. 8 can be performed by an automated folding machine in an automated environment.

Figure 9:
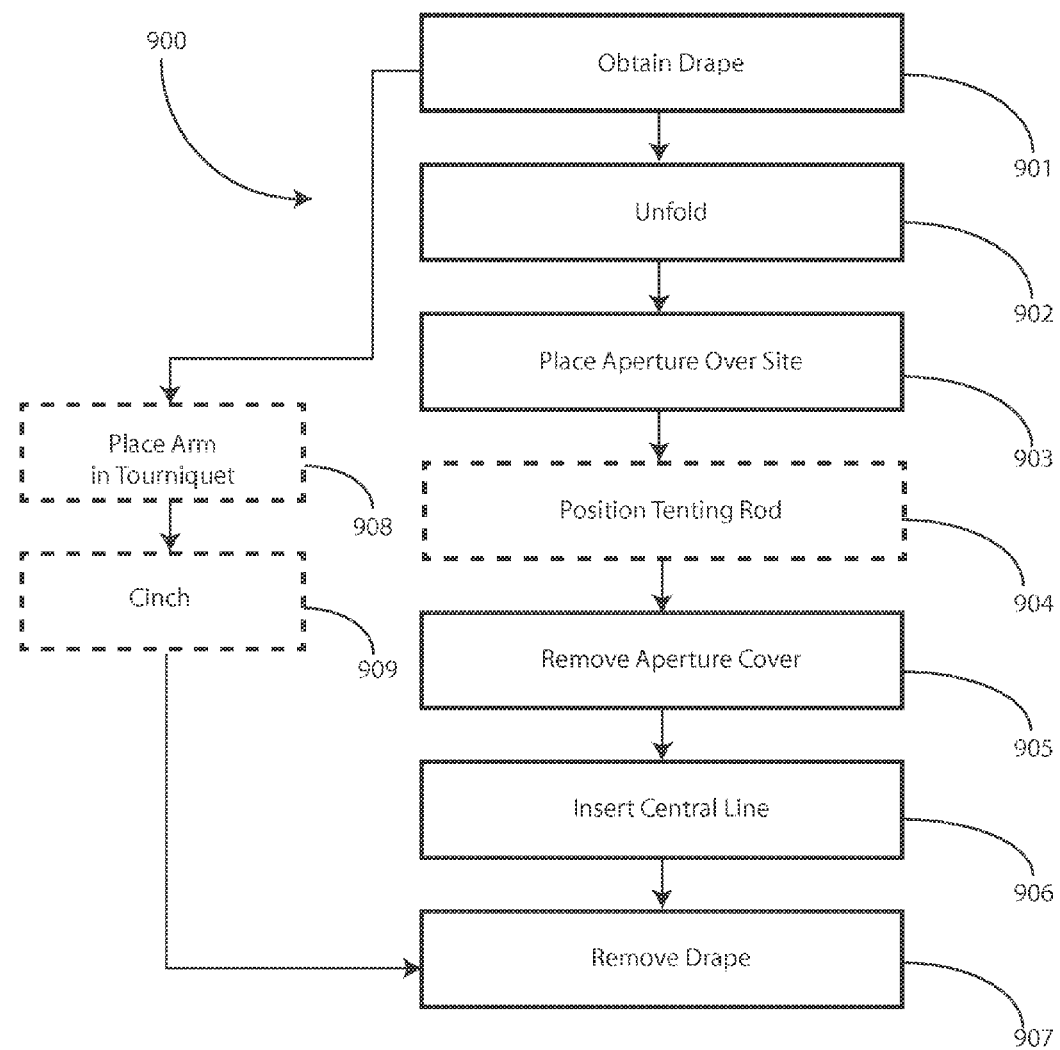
FIG. 9 illustrates a method of using medical drapes configured in accordance with one or more embodiments of the invention.

Turning to FIG. 9, a method 900 of using medical drapes configured in accordance with embodiments of the invention is shown. The steps have largely been described above, but will be briefly recounted here.

The method 900 begins at step 901, where a medical practitioner obtains a medical drape. In one embodiment, the medical drape includes a pellucid portion defining at least one peripherally inserted central catheter insertion aperture and a non-pellucid portion extending from the pellucid portion.

Figure 10:
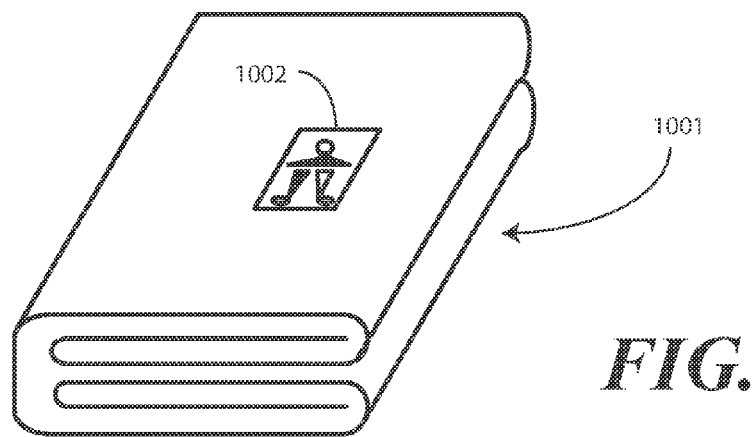
FIGS. 10-12 illustrate folding steps suitable for using or, in reverse order, making one or more drapes configured in accordance with embodiments of the invention.
Figure 10:
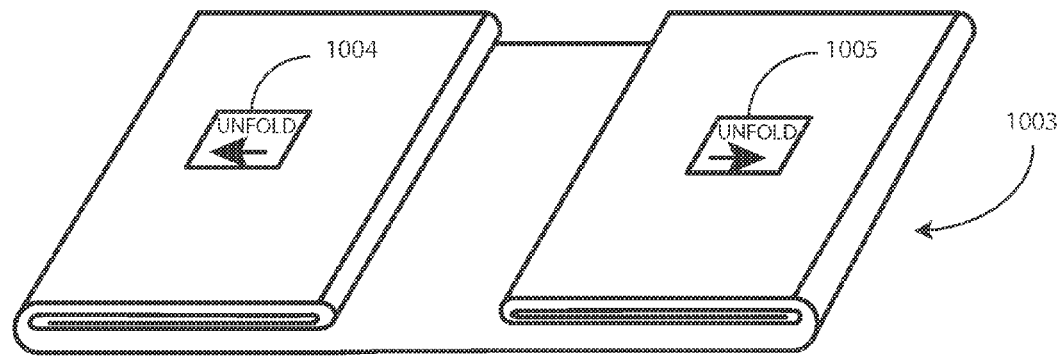
Figure 10:
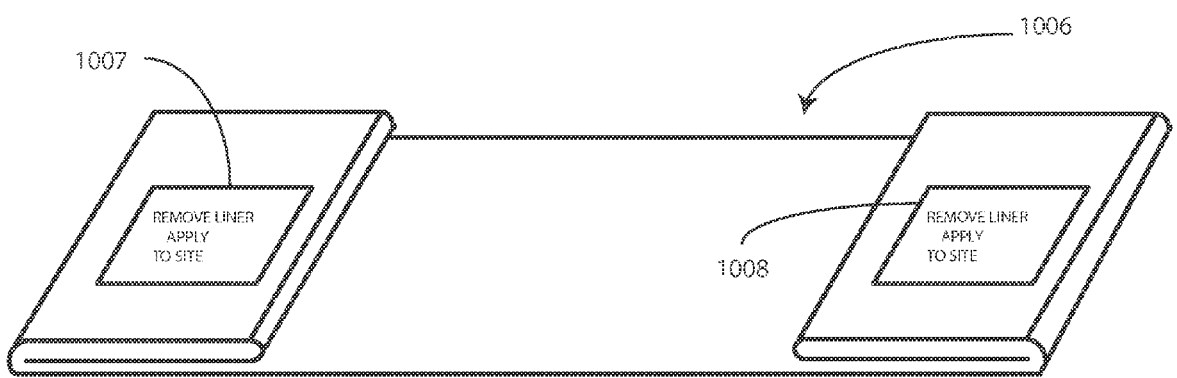
Figure 11:
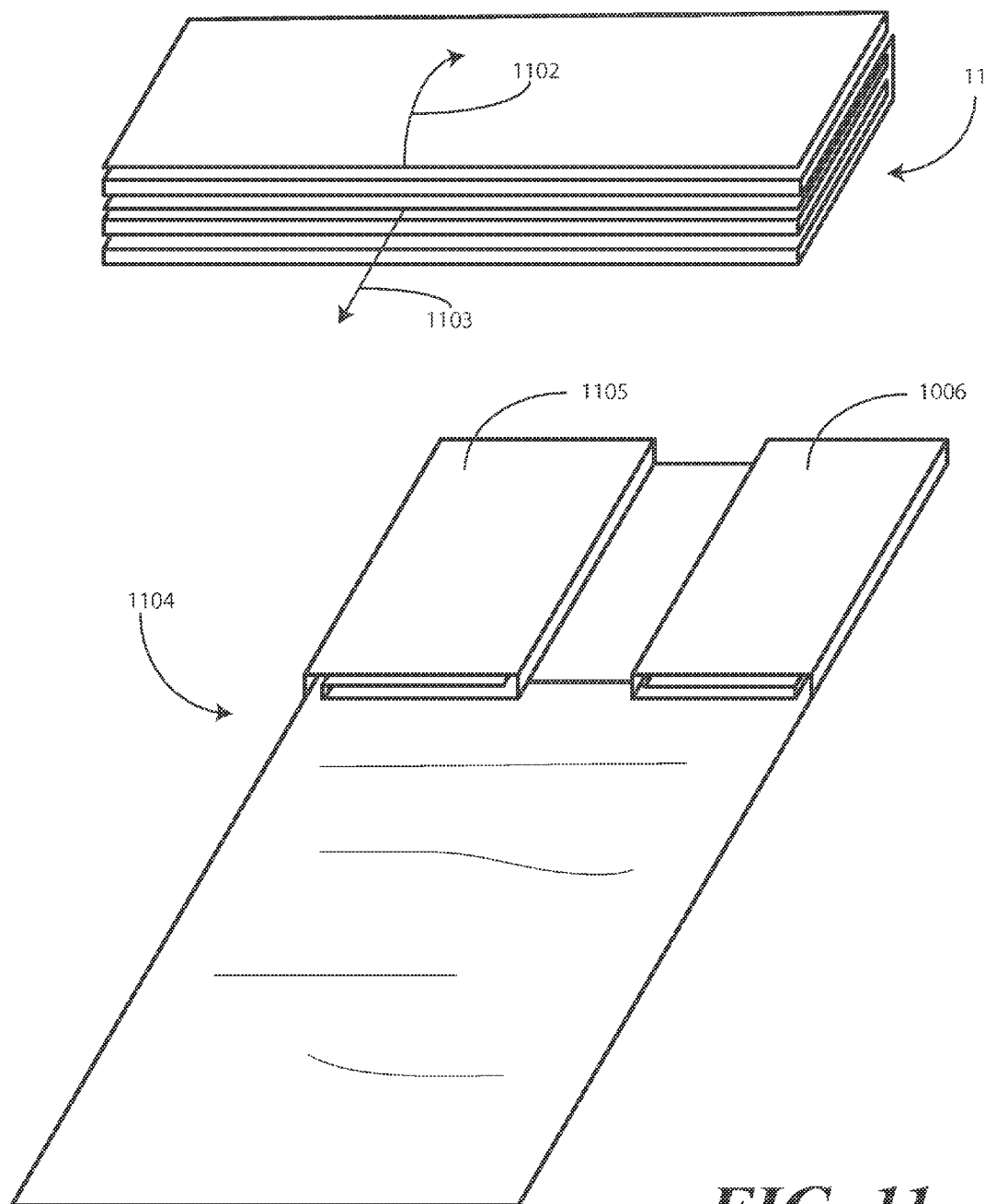
Figure 12:
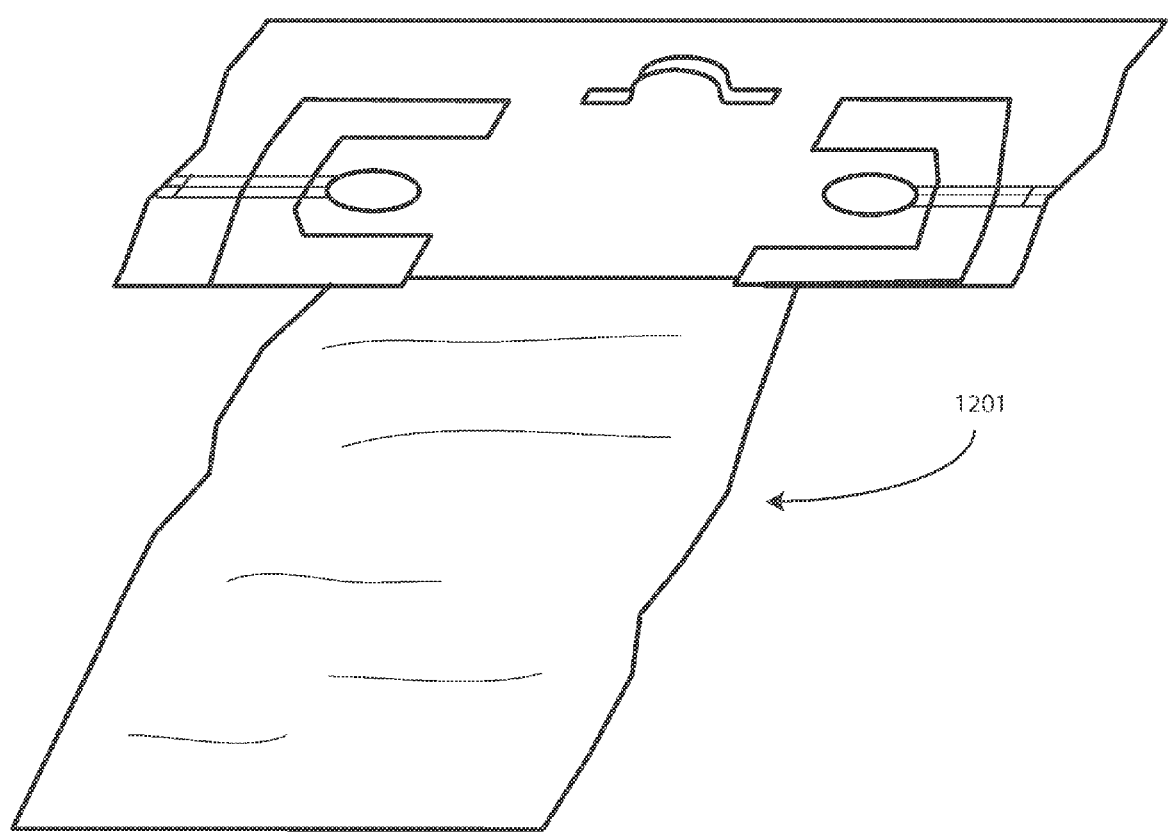

At step 902, the medical drape is unfolded across a patient. Where the medical drape was originally folded in accordance with the steps of FIG. 8, step 902 can include a reversal of that process. Turning briefly to FIGS. 10-12, the unfolding step 902 will be pictorially described. In one embodiment, the unfolding step 902 can be accomplished by a single person performing a catheterization procedure without compromising a required sterile field. Accordingly, the steps shown in FIGS. 10-12 will be described using a catheterization application. However, it will be clear to those of ordinary skill in the art that the steps could be readily adapted to other applications.

At step 1001, the a user places a folded drape 1079 on the chest of a patient. An optional indicator 1002, configured here as an ornamental stick figure, indicates which side of the folded drape 1079 should be toward the patient's head and which side of the folded drape 1079 should be towards the patient's feet. By orienting the ornamental stick figure with its head toward the patient's head, alignment of the folded drape 1079 is quickly and easily achieved.

At step 1003, a book fold of the folded drape 1079 is unfolded. In this illustrative embodiment, unfolding the book fold reveals to additional indicators 1004,1005 that instruct a user how to further open the drape by unfolding rolling folds.

When the rolling folds are unfolded, this reveals covering portions 1007,1008 disposed atop apertures or fenestrations at step 1006. In one embodiment, the covering portions 1007,1008 include instructions, such as "Remove Liner; Apply to Site." A user will generally remove one of the covering portions 1007,1008 and, where adhesive is provided, attach the drape to a patient's limb about a procedure site. Where the drape includes a tourniquet, as described in FIGS. 4-6 above, the tourniquet can be applied at this step 1006 as well.

At step 1101, the accordion folds of the upper portion and lower portion can be pulled to stretch the drape across the head and feet of the patient. In one embodiment, indicators are provided to show where and how the portions should be pulled 1102,1103. The result of this pulling process is shown at step 1104.

At step 1104, the remaining extensions of the upper portion of the drape can be unfolded to cover the limbs of the patient. The result is shown at step 1201. Where a tenting rod is included, step 1201 includes positioning the tenting rod such that at least some of the pellucid portion is away from a face of the patient. Where releasable covering covers the top of the aperture or fenestration, step 1201 can include removing the releasable covering. To preserve the sterile field, this is done in one embodiment after the insertion specialist has donned the proper gloves, gown, etc.

Turning now back to FIG. 9, the discussion of FIGS. 10-12 has described examples of step 903, placing the aperture or fenestration over the site, step 904, positioning the tenting rod, and step 905, removing the aperture or fenestration cover. The user or insertion specialist is then able to insert the peripherally inserted central catheter in the insertion site at step 906.

As noted above, and as described in FIGS. 10-12, in one or more embodiments the medical drape will include an integrated tourniquet. Where this is the case, optional steps for using the integrated tourniquet can be included. For example, at step 907 the patient's arm can be placed through the integrated sleeve. Where the tourniquet includes a coupler, step 907 can include fastening the coupler about the patient's limb. At step 908, at the appropriate time, the insertion specialist can cinch the tourniquet disposed within the sleeve by accessing ends of the tourniquet extending from a non-patient side of the medical drape.

Once the process is complete, the medical drape is removed from the patient at step 907. Where the medical drape includes a tool-less removal feature, this step 907 can include opening the tool-less removal feature as described above.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. For example, the upper portion of drapes can be configured to be opaque, while the lower portion is pellucid and defines one or more apertures for central catheter insertion, such as into a vein of one of the patient's legs.

Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A medical drape, comprising:
  a first portion and a second portion:
    the first portion wider than the second portion;
    the first portion pellucid;
    the second portion opaque; and
  a tourniquet integrated with the medical drape, the tourniquet enclosed within and passing through a sleeve on a patient side of the medical drape, with ends of the tourniquet that extend outwardly from a non-patient side of the medical drape;
  the first portion defining at least one aperture through which a peripherally inserted central catheter can be inserted into a patient when the medical drape is disposed atop the patient.

2. The medical drape of claim 1, wherein the medical drape is folded with a first rolling fold folding a first extended side of the first portion towards and over a center portion of the first portion, a second rolling fold folding a second extended side of the first portion towards and over the center portion.

3. The medical drape of claim 2, wherein the medical drape is further folded with an accordion fold folding the second portion.

4. The medical drape of claim 3, wherein the medical drape is further folded with an enclosing fold of at least some of the first portion about the accordion fold.

5. The medical drape of claim 1, the tourniquet comprising a coupler that bisects the sleeve.

6. The medical drape of claim 5, a first end of the sleeve attached to a first part the coupler.

7. The medical drape of claim 6, a second end of the sleeve attached to a second part of the coupler.

8. The medical drape of claim 1, further comprising a tool-less removal feature extending from an edge of the first portion to the at least one aperture.

9. The medical drape of claim 8, further comprising an indicator for indicating a starting point of the tool-less removal feature.

10. The medical drape of claim 1, wherein the first portion is configured for positioning over a brachial portion of the patient, a cubital portion of the patient, an antibrachial portion of the patient, or combinations thereof.

11. The medical drape of claim 1, further comprising a tenting bar disposed centrally along the first portion.

12. The medical drape of claim 1, further comprising a releasable covering disposed over the at least one aperture.

13. The medical drape of claim 1, wherein the first portion is manufactured from clear polyethylene and the second portion is manufactured from spunbond-meltblown-spunbond material.

14. The medical drape of claim 1, further comprising sealing features to prevent access to the tourniquet from the patient side.

15. The medical drape of claim 1, the tourniquet integrated with the first portion.

16. The medical drape of claim 1, the sleeve to prevent the tourniquet from compromising a sterile field on the patient side.

* * * * *